United States Patent
Hiltner et al.

(10) Patent No.: US 7,604,816 B2
(45) Date of Patent: Oct. 20, 2009

(54) BIO-ABSORBABLE COLLAGEN-BASED WOUND DRESSING

(75) Inventors: Claus M. Hiltner, Nuremberg (DE); Karl-Heinz Sorg, Neustadt (DE); Ton Pieter Alblas, Sprockhoevel (DE)

(73) Assignee: RESORBA Wundversorgung GmbH & Co. KG, Nuremberg (DE)

( * ) Notice: Subject to any disclaimer, the term of this patent is extended or adjusted under 35 U.S.C. 154(b) by 521 days.

(21) Appl. No.: 11/122,243

(22) Filed: May 5, 2005

(65) Prior Publication Data

US 2005/0260251 A1 Nov. 24, 2005

(30) Foreign Application Priority Data

May 7, 2004 (DE) .......................... 10 2004 022 645

(51) Int. Cl.
- *A61F 13/00* (2006.01)
- *A61F 2/00* (2006.01)
- *A61K 9/70* (2006.01)
- *A61L 15/00* (2006.01)
- *A61L 15/16* (2006.01)

(52) U.S. Cl. ...................... 424/422; 424/423; 424/443; 424/445; 424/447

(58) Field of Classification Search ................. 424/422, 424/423, 443, 445, 447
See application file for complete search history.

(56) References Cited

U.S. PATENT DOCUMENTS

| | | | |
|---|---|---|---|
| 4,193,813 A | * | 3/1980 | Chvapil ...................... 106/122 |
| 4,291,013 A | | 9/1981 | Wahlig et al. |
| 6,117,437 A | | 9/2000 | Roreger |
| 6,468,521 B1 | | 10/2002 | Pedersen et al. |
| 6,761,908 B1 | | 7/2004 | Roreger |
| 7,199,159 B2 | | 4/2007 | Potier et al. |
| 2004/0028722 A1 | | 2/2004 | Serafica et al. |

FOREIGN PATENT DOCUMENTS

| | | |
|---|---|---|
| DE | 199 62 221 A1 | 5/2001 |
| DE | 101 32 817 A1 | 1/2003 |
| EP | 0 314 109 A2 | 5/1989 |
| EP | 0562862 * | 3/1993 |
| WO | 00/33829 A1 | 6/2000 |
| WO | 03/004013 A1 | 1/2003 |
| WO | 2006/111347 A1 | 10/2006 |

OTHER PUBLICATIONS

Osada H, Tanaka H, Fujii TK, Tsunoda I, Yoshida T, Satoh K.,Clinical evaluation of a haemostatic and anti-adhesion preparation used to prevent post-surgical adhesion.J Int Med Res. Sep.-Oct. 1999;27(5):247-52.*
S. Coerper et al., Wound Healing and Wound Car 2004—State of the Art; ZFW No. 1/04, pp. 20-23; Summary in English.

* cited by examiner

*Primary Examiner*—Raymond J Henley, III
(74) *Attorney, Agent, or Firm*—David S. Safran; Roberts Mlotkowski Safran & Cole, P.C.

(57) ABSTRACT

A collagen-based bio-absorbable wound dressing which contains a linear polymer biguanide and/or a water-soluble salt thereof. The biguanide is preferably polyhexamethylene biguanide. The bio-absorbable wound dressing has a long residence time in the body, is extremely well tolerated and leads to rapid and uncomplicated wound healing with clearly reduced infection risk.

20 Claims, No Drawings

BIO-ABSORBABLE COLLAGEN-BASED WOUND DRESSING

BACKGROUND OF THE INVENTION

1. Field of Invention

The invention relates to a collagen-based bio-absorbable wound dressing. Collagen as the albuminoid protein of the connective tissue is a component of the bodies of mammals. Collagen is ordinarily obtained from the tendons and/or skins of cattle, swine or horses. Depending on its origin and its structure, collagen is divided into different types. All types of collagen share a triple helix structure which is formed from three polypeptide chains.

2. Description of Related Art

As an endogenous material collagen is outstandingly well tolerated by the body and can be easily absorbed, and in this respect, is far superior to exogenous, synthetic materials such as cellulose. Accordingly, collagen has long been used as a wound dressing for local hemostasis, as a material for coating of tissue and bone defects, as a skin replacement in lesions and as a skin covering for large area burns. Collagen is also used as a absorbable suture material.

In addition to its good tolerance by the body and absorbability, collagen has the advantage compared to other materials that it acts hemostatically. Therefore, one application of collagen lies in dressing of wounds, especially those wounds in which some of the dermal structures or also the structures which lie under the skin have been involved. Collagen is used to treat both acute and chronic wounds. Chronic wounds are conventionally those which do not exhibit a tendency to healing even after a period of 4 to 6 weeks. Examples of chronic wounds are:

ulcus cruris (for example, due to venous or arterial conditions)

diabetic foot syndrome decubitus, i.e., an area of the skin in which, due to excess pressure, a wound has formed, with necrosis and ulceration, often with the involvement of dermal and subdermal tissue.

It is known that collagen can promote healing of acute and chronic wounds. In a first step, thrombocyte aggregation occurs on the collagen fibrils. The blood flow in the wound is stanched and the wound closed by collagen gel. Moreover, the collagen interacts with structures of the vascular wall and the connective tissue proteins and activates body cells which are involved in wound healing, especially the fibroblasts. In this way, the strength of the coagulation is increased. In the last stage of wound healing, the collagen is absorbed by the body by immigrated macrophages and collagenase, the wound is filled with endogenous material, and the wound surface is finally closed and smoothed.

However, wound healing can be dramatically adversely affected or prevented by wound infection, among others. Therefore, to reduce infections, wound dressings have been proposed which contain a microbicidal substance. U.S. Pat. No. 6,468,521, for example, describes a wound dressing with hydrophilic polymer carrier which is impregnated with a silver-amine complex. The silver compound has bacteriostatic and fungistatic properties. Among others, collagen is named as the carrier material. However, apparently, these silver-containing bandages are problematic in use (compare, S. Coerper, G. Gottwald, S. Beckert and H. D. Becker, "Wound healing and treatment 2004—Current status" in ZfW No. 1/04, pp. 20 to 23; page 21, right column).

While good absorbability of collagen can in general be regarded as an advantage, overly rapid absorption of collagen in wound treatment can also entail disadvantages. The speed of absorption of collagen in the body, on the one hand, depends on its structure and especially the degree of crosslinking but, on the other hand, is decisively influenced by the application site. In tissue which is well supplied with blood, for example, collagen can be completely dissolved within 2 to 3 days, while under other conditions, absorption can take 2 to 6 weeks. German Patent DE 19503336 and corresponding U.S. Pat. No. 6,117,437, for example, describe that a drug preparation with a depository effect in which the drug is administered on a collagen vehicle which is mixed with chlorohexidine hydrochloride completely decomposes in the body after 30 minutes. In wound dressings, however, it is often desirable that they remain on the wound for at least 72 hours. Overly frequent changing of the bandage entails not only the danger that the wound will be torn open again, but also increases the danger of infection. Therefore, there is a demand for a wound dressing of collagen which is not completely absorbed even in tissue, with good blood supply, over an interval of at least 3 days.

German Patent Application DE 10132817 A1 discloses a wound treatment agent in the form of a solution or a gel that contains, in aqueous solution, polyhexamethylene biguanide and at least one surfactant. The surfactant is a glycine derivative and/or a sulfosuccinate and/or an amide based on an unbranched fatty acid. The surfactant is preferably a betaine and, in particular, an amidoalkyl betaine of a fatty acid.

SUMMARY OF THE INVENTION

A primary object of the present invention is, accordingly, to provide a bio-absorbable wound dressing based on collagen which has good body toleration and good absorbability, yet will not be completely dissolved in the body over a period of a few days and will ensure reliable protection against infections.

This object is achieved by providing a collagen-based, bio-absorbable wound dressing that contains a linear polymer biguanide and/or a water-soluble salt thereof.

DETAILED DESCRIPTION OF THE INVENTION

The invention relates to a bio-absorbable collagen-based wound dressing which is characterized in that it contains a linear polymer biguanide and/or a water-soluble salt thereof. Polyhexamethylene biguanide (PHMB) is used as the preferred biguanide.

Linear polymer biguanides and especially polyhexamethylene biguanide are well tolerated compounds which are known for their good microbicidal action. They have a broad action spectrum against a host of bacteria, fungi and even some viruses. Linear polymer biguanides are already highly effective in a low concentration, and moreover, can be used over a wide pH range. They do not lose their microbicidal activity even with high protein loading and can be used without loss of effect in the presence of blood and protein; this is a major advantage especially in wound treatment. Also, the linear polymer biguanides in amounts which are conventionally used are essentially not cytotoxic. This is very advantageous for a wound dressing since, in this way, the formation of granulation tissue and thus ultimately epithelialization of the wound are not disrupted.

Within the framework of the invention, all linear polymer biguanides which have a germicidal action can be used. However, the preferred biguanide is polyhexamethylene biguanide (PHMB). Like all other biguanides, it can be used as such or in the form of a water-soluble salt. Here, the hydrochloride is preferable which is available, for example, in the form of a 20% solution under the name Vantocil® IB or Cosmocil® CQ from Avecia, Manchester, GB, or Frankfurt/Main, DE. Whenever biguanide or PHMB is discussed in general below, the salts of these compounds will always be intended at the same time. The molecular weight ranges in which the biguanides can be used are not especially limited. Rather, all these compounds with the molecular weights which have been conventional to date can be used. In the case of PHMB, the molecular weight lies, for example, in the range from roughly 1500 to 15000. Molecular weights of PHMB under 5000 and especially under 2900 are preferred.

Incorporation of the linear polymer biguanide into the collagen can take place in different ways. It can take place during processing of the collagen into certain forms of the bio-absorbable wound dressing or following it. The biguanide can be incorporated into the collagen as a solid or in the form of a solution in a suitable solvent, such as, for example, water. The solvent can then be evaporated from the bio-absorbable wound dressing or can remain in it, for example, to yield a moist wound dressing.

The linear polymer biguanides or their salts are easily compatible with collagen. It was surprisingly found that the addition of the biguanide can distinctly slow down absorption of the collagen in the body. This can presumably be attributed to the fact that the bactericidal action of the biguanide prevents the spread of microorganisms which produce the enzyme collagenase. Collagenase causes breakdown of the collagen which thus quickly loses it consistency and gels. The loss of consistency of the collagen in turn leads to its no longer being able to satisfactorily perform its function as a wound dressing. The presence of the linear polymer biguanide with its bactericidal action in the absorbable wound dressing as claimed in the invention conversely slows down the decomposition of the collagen without completely stopping its absorption in the body. The loss of structure of the material therefore occurs much later. Even if the bio-absorbable wound dressing of the invention is used in tissue with good blood flow, it can easily remain there for 72 hours or longer without being completely absorbed during this time.

The microbicidal action which is imparted to the bio-absorbable wound dressing of the invention by the content of a linear polymer biguanide has a beneficial effect on the tissue with which the bio-absorbable wound dressing comes in contact. On the one hand, therapeutic support leads to a distinct acceleration of healing in infected wounds, and on the other hand, the action is prophylactic and prevents the infection of uninfected wounds or prevents manifest infection in contaminated and infected wounds.

The prophylactic and/or therapeutic action of the bio-absorbable wound dressing as in accordance with the invention can be further increased by having it contain at least one tenside, i.e. a surface active agent. The use of a tenside leads to a reduction of the surface tension in the tissue with which the bio-absorbable wound dressing is in contact. Biofilms formed on the tissue are dissolved in this way. Moreover, for cleaned tissue on which there is no biofilm, such a biofilm is prevented from forming. Biofilms acquire special importance in the case of wound treatment. Biofilms are complex structures which form when microorganisms settle on a surface, a multicellular structure forming with the indicated cells in an extracellular biopolymer matrix which has been produced by these cells. These biofilms like to form on existing wound coverings which offer good growth conditions to germs from skin flora and also pathogenic germs and greatly delay wound healing. The spread of wound infections conventionally takes place over these wound coverings on which the microorganisms multiply. The presence of at least one tenside in the bio-absorbable wound dressing of the invention, conversely, deters the formation and spread of these biofilms and wound coverings, and thus, greatly reduces the danger of infection.

The tenside in the bio-absorbable wound dressing in accordance with the invention is preferably a nonionic tenside, an amphotenside or a combination thereof. These tensides do not adversely affect the antimicrobial action of the linear polymer biguanide, while in anionic tensides there is this danger. Combinations of biguanides with tensides are fundamentally known in the prior art. Often, for example, PHMB is used in combination with polyethylene glycol. This combination can likewise be used within the framework of the invention. However, it is preferred that a linear polymer biguanide and especially PHMB be used in combination with a tenside, as is disclosed in the above mentioned German Patent Application DE 10132817 A1. The tensides named there are especially glycine derivatives, and of them, the amidoalkyl betaines of a fatty acid are preferred. Undecylene amidoalkyl betaines, cocamidoalkyl betaines, lauramidoalkyl betaines or ricinolamidoalkyl betaines are especially suited as tensides for use in the bio-absorbable wound dressing in accordance with the present invention, the alkyl residue preferably being ethyl or propyl. Currently, it is especially preferred that a combination of PHMB or its hydrochloride with undecylenic acid amidopropyl betaine be used as the tenside. An aqueous solution of these components is available, for example, under the name Prontosan®. Basically, the same as was explained for the polymer biguanide applies to the incorporation of the tenside into the bio-absorbable wound dressing.

The collagen-based bio-absorbable wound dressing of the invention can be fundamentally used in all applications in which bio-absorbable wound dressings have been used to date. These applications include the initially mentioned uses as a dry or wet wound dressing. Depending on the type of use planned, the origin, type and preparation form of the collagen can be chosen in the conventional manner. Production takes place, basically, in the manner described in the prior art from animal starting material, for example, from the tendons and/or skin of cattle, swine or horses, equine collagen being preferred within the framework of the invention. The type of collagen used is likewise not especially limited, but types I, III and X are especially preferred.

The density and degree of cross-linking of the collagen are likewise chosen depending on the application requirement. As already mentioned, an increased degree of cross-linking slows down the absorption of the collagen in the body. Suitable densities of the collagen are within 1 and 22 $mg/cm^3$ and especially between 6 and 12 $mg/cm^3$.

The preparation form of the collagen likewise corresponds to that which is already known from the prior art. For example, the collagen can be present in the form of a porous sponge, a foil, a film, a membrane, a nonwoven or a tamponade. All these preparation forms can be produced in the manner which is conventional in the prior art. Before use, the collagen material is preferably sterilized in the known manner. Sterilization with ethylene oxide or gamma radiation, preferably with 28 kGray±10%, is especially suitable for this purpose. The size of the preparation forms depends on the intended use. Conventionally, the collagen material will have a thickness between 0.1 and 20 mm, and preferably, between 2 and 7 mm.

The wound dressing preferably has an absorption capacity for liquid of 0.1 $ml/cm^3$ to 1.0 $ml/cm^3$. A liquid absorption capacity in the range from 0.2 $ml/cm^3$ to 0.5 $ml/cm^3$ is especially preferred.

The bio-absorbable wound dressing in accordance with the invention can be used both as a dry and also a wet wound dressing. In the latter case, which is preferable, production feasibly takes place in that the collagen material is impregnated with an aqueous solution of the linear polymer biguanide, and optionally, the tenside. To do this, the indicated components are dissolved in purified and sterilized water in the amount suited for the intended action. Here, polyhexamethylene biguanide, which is especially preferred as the biguanide, is feasibly contained in a concentration from 0.01 to 1% by weight, especially 0.01 to 0.3% by weight, and preferably, 0.025 to 0.1% by weight in the aqueous solution. The amphotenside, and here especially, the undecylenic acid amidopropyl betaine in an aqueous solution preferably has a concentration from 0.01 to 1.5% by weight, especially 0.01 to 0.4% by weight, and preferably, 0.025 to 0.1% by weight.

Overall, the concentration of the polyhexamethylene biguanide in the collagen-based wound dressing of the invention is dimensioned, preferably, according to the intended indication. The concentration ranges are not especially limited here, since with an excess of the polyhexamethylene biguanide almost no adverse effects are observed. Therefore, in general, it must simply be watched that the amount of polyhexamethylene biguanide is enough to achieve the desired prophylactic and/or therapeutic action. The concentration of the tenside in the wound dressing is not especially limited either. The amount is chosen such that the desired reduction of the surface tension in the area of the body to be treated is achieved.

Compared to other microbicidal agents, linear polymer biguanides, such as especially polyhexamethylene biguanide, have the advantage that they can be used over a wide pH range without losing their bactericidal or fungicidal effectiveness. Especially good effectiveness for wound healing is achieved when the wet wound dressing of the invention is adjusted such that the pH value lies in the range from 3.5 to 6.5.

In addition to the linear polymer biguanide, and optionally a tenside, the bio-absorbable wound dressing in accordance with the invention can contain other components, such as, especially, a pharmaceutical agent. The possibility of using collagen as a vehicle for pharmaceutical agents has basically already been described (compare, the initially mentioned DE 19503336 C2 and corresponding U.S. Pat. No. 6,117,437). The linear polymer biguanides used in the collagen material in accordance with the invention have the advantage that they are compatible with a host of pharmaceutical agents and do not adversely affect their effectiveness. Agents which promote wound healing and/or reduce the danger of wound infection are preferably used. For example, for these agents growth factors, such as PDGF (platelet derived growth factor) or EGF (epidermal growth factor), cytokines, hyaluronic acid or antibiotics can be named. The addition of these agents to the bio-absorbable wound dressing of the invention takes place in the conventional pharmaceutically effective doses. Incorporation can take place as in the case of the biguanide or the tenside.

The preparation of the tissue with which the bio-absorbable wound dressing as in accordance with the invention comes into contact can take place in the conventional manner. Wounds are preferably debrided beforehand and thoroughly washed, the use of PHMB-containing wound flushing solutions, such as Prontosan® being especially recommended. The wound dressing of the invention can remain for 72 hours or longer on the wound due to the high absorption resistance. Since the infection risk is minimal and the wound dressing gels over time and is almost completely decomposed to short-chain peptides, it is not necessary at all to remove the old wound dressing from the wound. Rather another wound dressing in accordance with the invention can be applied to/over the old one. If the old wound dressing is to be removed, this can, if necessary, take place using PHMB-containing or other suitable wound flushing solution. Then, the wound is preferably cleaned again with the wound flushing solution before the new wound dressing is applied.

The invention is explained in further detail below using a production example for a wound dressing.

EXAMPLE 1

Production of a Collagen-Based Wound Dressing a) Production of the Collagen Material Fresh horse tendons from which all pigment layers and muscle residues have been removed are homogenized. An amount which corresponds to 100 g dry weight is extracted for 24 hours in 3 liters of 0.05 M citrate buffer (pH 3.7) and then dialyzed for 12 hours against 1% acetic acid. The tissue which is suspended in 3 liters of 1% acetic acid is incubated for 48 hours at 15° C. with continuous stirring with pepsin in a collagen to pepsin ratio of 50:1.

The batch is diluted to 5 liters with 1% acetic acid and the undissolved tendon fragments are removed by centrifuging. The viscous collagen solution is dialyzed against alkalized tap water (pH 8.0) and then sharply centrifuged. The residue is dissolved again in 5 liters of 1% acetic acid and dialyzed. This process is repeated several times. Then a 1.5% collagen solution is produced by means of 0.05% acetic acid.

b) Production of the Agent-Containing Wound Dressing

The PHMB, and optionally, the tenside, are incorporated into the collagen solution described under a) in the corresponding amount. This viscous solution is dried by lyophilization or another method which corresponds to the prior art by removing the moisture. Last, the sponge is packaged and sterilized by ethylene oxide or gamma radiation.

What is claimed is:

1. Bio-absorbable wound dressing, comprising a collagen-based material which contains at least one of a linear polymer biguanide and a water-soluble salt thereof.

2. Bio-absorbable wound dressing as claimed in claim 1, wherein the linear polymer biguanide is polyhexamethylene biguanide.

3. Bio-absorbable wound dressing as claimed in claim 1, wherein collagen-based material also contains at least one tenside.

4. Bio-absorbable wound dressing as claimed in claim 3, wherein the tenside is at least one of a nonionic tenside and amphotenside.

5. Bio-absorbable wound dressing as claimed in claim 4, wherein the tenside is a glycine derivative.

6. Bio-absorbable wound dressing as claimed in claim 5, wherein the tenside is an amidoalkyl betaine of a fatty acid.

7. Bio-absorbable wound dressing as claimed in claim 6, wherein the glycine derivative is selected from the group consisting of undecylene amidoalkyl betaine, cocamidoalkyl betaine, lauramidoalkyl betaine and ricinolamidoalkyl betaine.

8. Bio-absorbable wound dressing as claimed in claim 1, wherein the collagen is an equine collagen.

9. Bio-absorbable wound dressing as claimed in claim 1, wherein the collagen is of type I, III, or X.

10. Bio-absorbable wound dressing as claimed in claim 1, wherein the collagen has a density from 1 and 22 mg/cm$^3$.

11. Bio-absorbable wound dressing as claimed in claim 1, wherein the collagen has a density from 6 to 12 mg/cm$^3$.

12. Bio-absorbable wound dressing as claimed in claim 1, wherein the collagen is in the form of one of a sponge, a foil, a film, a membrane, a nonwoven and a tamponade.

13. Bio-absorbable wound dressing as claimed in claim 1, wherein the collagen has a liquid absorption capacity of 0.1 ml/cm$^3$ to 1 ml/cm$^3$.

14. Bio-absorbable wound dressing as claimed in claim 1, wherein the collagen has a liquid absorption capacity of from 0.2 ml/cm$^3$ to 0.5 ml/cm$^3$.

15. Bio-absorbable wound dressing as claimed in claim 1, wherein the collagen is impregnated with an aqueous solution of the linear polymer biguanide.

16. Bio-absorbable wound dressing as claimed in claim 15, wherein the collagen also contains a tenside.

17. Bio-absorbable wound dressing as claimed in claim 16, wherein the solution contains
0.01 to 1.0% by weight polyhexamethylene biguanide and
0.01 to 1.5% by weight of an amphotenside.

18. Bio-absorbable wound dressing as claimed in claim 1, wherein it is adjusted as a wet wound dressing to a pH of from 3.5 to 6.5.

19. Bio-absorbable wound dressing as claimed in claim 1, wherein the collagen contains at least one pharmaceutical agent.

20. Bio-absorbable wound dressing as claimed in claim 14, wherein the at least one pharmaceutical agent is selected from the group consisting of a growth factor, a cytokine, hyaluronic acid and an antibiotic.

* * * * *